United States Patent
Conrad et al.

(10) Patent No.: US 6,455,000 B1
(45) Date of Patent: Sep. 24, 2002

(54) METHOD AND APPARATUS FOR MEASURING THE CONCENTRATION OF A GAS

(75) Inventors: Wayne Ernest Conrad; Helmut Gerhard Conrad; Ted Szylowiec, all of Hampton (CA)

(73) Assignee: Fantom Technologies Inc., Welland (CA)

( * ) Notice: Subject to any disclaimer, the term of this patent is extended or adjusted under 35 U.S.C. 154(b) by 0 days.

(21) Appl. No.: 09/350,929

(22) Filed: Jul. 12, 1999

(51) Int. Cl.[7] .............................................. G01N 25/58
(52) U.S. Cl. ...................... 422/50; 422/51; 436/147; 73/23.2; 73/23.25; 73/25.01
(58) Field of Search ...................... 436/147, 91, 52; 73/514.18, 25.01, 24.01, 105, 1, 23, 204.26, 862.64

(56) References Cited

U.S. PATENT DOCUMENTS

| 4,011,745 | A | * | 3/1977 | Gatos et al. ................... 73/23 |
| 4,928,513 | A | * | 5/1990 | Sugihara et al. ................. 73/1 |
| 4,966,037 | A | * | 10/1990 | Sumner et al. ........... 73/204.26 |
| 5,079,958 | A | * | 1/1992 | Takase et al. ............. 73/862.64 |
| 5,167,927 | A | | 12/1992 | Karlson ........................ 422/90 |
| 5,719,324 | A | * | 2/1998 | Thundat et al. ............. 73/24.01 |
| 5,763,782 | A | * | 6/1998 | Moore et al. ............. 73/514.18 |
| 5,804,703 | A | * | 9/1998 | Wind et al. ................. 73/25.01 |
| 5,863,803 | A | * | 1/1999 | Zanini-Fisher et al. ...... 436/147 |
| 6,006,593 | A | * | 12/1999 | Yamanaka .................... 73/105 |
| 6,077,712 | A | * | 6/2000 | Livingston .................... 436/91 |
| 6,096,559 | A | * | 8/2000 | Thundat et al. ............. 436/147 |
| 6,171,879 | B1 | * | 1/2001 | Chan et al. .................... 438/52 |

* cited by examiner

Primary Examiner—Jill Warden
Assistant Examiner—Brian Sines
(74) Attorney, Agent, or Firm—Philip C. Mendes da Costa; Bereskin & Parr

(57) ABSTRACT

A method and apparatus using thermomechanical means for signalling the concentration of a reactive gas is disclosed. The thermomechanical means uses movement of a mechanical member to produce a signal corresponding to the concentration of the reactive gas in a gas stream. The method and apparatus may include means for converting a specific gas in a gas stream to a reactive gas. The apparatus may then provide an analog readout of the concentration of the specific gas.

43 Claims, 3 Drawing Sheets

METHOD AND APPARATUS FOR MEASURING THE CONCENTRATION OF A GAS

FIELD OF THE INVENTION

This invention relates to a thermomechanical method and apparatus for measuring the concentration of a gas and in particular a reactive gas (i.e. gasses that may be reacted to produce by-products and which produce heat or remove heat from a system as a result of the reaction). Examples of such gasses include ozone, oxygen, nitrogen or oxides of nitrogen, and the like. The method and apparatus may function independent of the temperature of a gas mixture containing the reactive gas.

BACKGROUND OF THE INVENTION

There are instruments available that measure ozone concentration in a gas mixture. One such instrument is disclosed in U.S. Pat. No. 5,167,927, Karlson. This Pat. discloses an apparatus that measures heat energy released when a reactive gas is catalytically converted to a different gas, for example using a catalyst to convert ozone to oxygen. In particular, Karlson discloses an apparatus that directs a stream of a gas mixture containing ozone against thermally conducting heat sinked plates on opposite sides of an axis of the stream with the plates extending upstream at an acute angle to the axis. One plate carries on its upstream facing a coating including a catalyst for ozone, while the other plate includes no catalyst on its upstream facing. A sensor is provided for measuring the temperatures of the respective plates. A separate chamber is provided having a similar arrangement of plates. The ozone concentration of the gas is electronically measured as the resistance difference of the two plates in each chamber.

One disadvantage of Karlson is that the flow of the gas mixture stream in Karlson is important to the instruments sensitivity, and is electronically controlled to be constant for each sample of gas mixture measured. A further disadvantage is that the instrument's sensitivity and time constant is dependant on the velocity of the sample flow through the instrument, its electronic time constant and its thermal time constant.

There is also a need for an inexpensive, durable and easily calibrated apparatus for determining the concentration of reactive gasses such as ozone.

SUMMARY OF THE INVENTION

In accordance with the instant invention a thermochemical means is used to produce movement of a member which is drivingly connected to an indicator. In a preferred embodiment, the indicator is associated with an analog scale to thereby provide a readout of the concentration of a gas without the use of any electronic monitoring means. In this way a simple mechanical sensor for reactive gasses such as ozone and $NO_X$ can be produced.

In accordance with the instant invention, there is provided a method of measuring a change in heat produced during conversion of a reactive gas by a catalyst to produce a by-product, the method comprising the steps of:

(a) using a first temperature sensor which undergoes movement with changes in temperature to which it is exposed to produce. a first measurement representing the initial temperature of the gas mixture;

(b) exposing at least a portion of the gas mixture to the catalyst to produce a change in heat;

(c) using a second temperature sensor which undergoes movement with changes in temperature to which it is exposed to produce a second measurement representing the change in heat due to the portion of the gas stream being exposed to the catalyst; and, (d) combining the first measurement and the second measurement to determine a differential measurement representing a measurement of the heat change during conversion of the reactive gas by the catalyst.

In one embodiment, the method further comprises the step of calibrating the first and second temperature sensors so that when there is no reactive gas within the gas mixture the first measurement and the second measurement produce a differential measurement which is a fixed measurement and is preferably zero.

In another embodiment, the differential measurement is calibrated to represent the concentration of the reactive gas within the gas mixture and the method further comprises the step of reading the concentration of the reactive gas from a display of the differential measurement.

In another embodiment, the first temperature sensor is positioned in a first chamber and the second temperature sensor is positioned in a second chamber and the method further comprises dividing the gas stream into two portions and introducing a portion into each chamber.

In another embodiment, the first temperature sensor is positioned in a first chamber and the second temperature sensor is positioned in a second chamber and the method further comprises sequentially passing the gas stream through the first chamber and then the second chamber.

In another embodiment, the method further comprises first converting. a specific gas in a gas stream to produce the reactive gas. Thus, the method may be used to measure the concentration of a non-reactive gas (eg. oxygen or nitrogen).

In another embodiment, the first measurement and the second measurement are signals produced by the temperature sensors and the method further comprises reading the first and second measurements prior to combining them to determine a differential measurement.

In another embodiment, the first measurement and the second measurement are opposed forces which are exerted on a member and the net movement of the member produces the differential measurement and the method further comprises reading the differential measurement.

In accordance with another aspect of the instant invention, there is also provided a method of measuring a change in heat produced during conversion of a reactive gas by a catalyst to a by-product, the method comprising the steps of:

(a) exposing the gas mixture to the catalyst to generate heat; and, (b) using a temperature sensor which undergoes movement with changes in temperature to which it is exposed to produce a measurement representing the change in heat due to the gas stream being exposed to the catalyst.

In one embodiment, the method further comprises the step of calibrating the temperature sensor so that at ambient conditions when there is no reactive gas within the gas mixture the measurement is constant and preferably is zero. The measurement may be calibrated to represent the concentration of the reactive gas within the gas mixture and the method further comprises the step of reading the concentration of the reactive gas from a display of the measurement.

In another embodiment, the method further comprises first converting a specific gas in a gas stream to produce the reactive gas.

In another embodiment, the measurement is a force which is exerted on a member and the movement of the member produces a corresponding measurement and the method further comprises reading the corresponding measurement.

In accordance with another aspect of the instant invention, there is also provided an apparatus comprising:

(a) a catalyst positioned in an air flow path of a gas mixture containing a reactive gas, the reactive gas undergoing a reaction to produce a by-product and a change in heat upon exposure to the catalyst; and, (b) a reacted gas temperature sensor which undergoes movement with changes in temperature to which it is exposed to produce a reacted gas measurement representing the change in heat produced by the reaction of the reactive gas.

In one embodiment, the measurement is calibrated to represent the concentration of the reactive gas within the gas mixture.

In another embodiment, the temperature sensor includes an indicator, the apparatus further comprises an analog display which is calibrated to represent the concentration of the reactive gas within the gas mixture, and the measurement comprises the movement of the indicator due to the change in temperature of the temperature sensor. Alternately, the measurement may be an electronic signal. However in this alternate embodiment, the sensing means still uses a thermomechanical member. The difference resides in the type of signal which is produced.

In another embodiment, the gas mixture comprises a specific gas and the apparatus further comprises a generator positioned upstream of the catalyst for converting at least a portion of the specific gas to the reactive gas.

In another embodiment, the apparatus further comprises:

(a) an ambient temperature chamber for receiving at least a portion of the gas mixture, the ambient temperature chamber having an ambient temperature sensor which undergoes movement with changes in temperature to which it is exposed to produce an ambient measurement representing the ambient temperature of the gas mixture;

(b) a second chamber in which the reacted gas temperature sensor is positioned; and, (c) a differentiator to produce a differential measurement that represents a measurement of the heat generated during conversion of the reactive gas by the catalyst independent of the ambient temperature of the gas mixture containing the reactive gas.

The ambient and reacted gas temperature sensors may be calibrated so that when there is no reactive gas within the gas mixture the ambient measurement and the reacted gas measurement produce a differential measurement that is constant and, preferably is zero. Further, the differential measurement may be calibrated to represent the concentration of the reactive gas within the gas mixture. The apparatus may include a divider having two outlets, one of which is in air flow communication with the ambient chamber and the other of which is in air flow communication with the reacted gas chamber. Alternately, the apparatus may have an air inlet to the ambient chamber, a passageway connecting the chambers in air flow communication, and an air outlet from the reacted gas chamber, whereby the gas mixture passes sequentially through the ambient chamber and then the reacted gas chamber.

The measurements may be one or more electronic signals or they may be opposed forces which are exerted on the differentiator to produce a net movement of the differentiator which is the differential measurement. The apparatus may further comprise an analog display and an indicator associated with the analog display and drivienly connected to one of the temperature sensors or the differentiator.

In accordance with another aspect of the instant invention, there is also provided an apparatus comprising:

(a) a catalyst positioned in an air flow path of a gas mixture containing a reactive gas, the reactive gas undergoing a reaction to produce a by-product and a change in heat upon exposure to the catalyst;

(b) a reacted gas thermomechanical sensing means for producing a movement of at least a portion of the sensing means due to changes in temperature to which it is exposed; and, (c) indicating means for providing a readout corresponding to the concentration of the reactive gas in the gas mixture.

In one embodiment, the gas mixture comprises a specific gas and the apparatus further comprises a means positioned upstream of the catalyst for converting at least a portion of the specific gas to the reactive gas.

In another embodiment, the apparatus further comprises an ambient thermomechanical sensing means for contacting at least a portion of the gas mixture which has not been exposed to the catalyst and producing movement of at least a portion of the sensing means due to changes in temperature to which it is exposed.

In another embodiment, the movement of each sensing means produces electronic signals which are combined by the indicating means to produce the readout.

In another embodiment, the movement of each sensing means produces opposed forces which cause the indicating means to move by a net amount to provide the readout which preferably provides a readout on an analog scale.

In another embodiment, the gas mixture comprises a specific gas and the apparatus further comprises a means positioned upstream of the catalyst for converting at least a portion of the specific gas to the reactive gas.

BRIEF DESCRIPTION OF THE DRAWING FIGURES

For a better understanding of the present invention and to show more clearly how it would be carried into effect, reference will now be made, by way of example, to the accompanying drawings that show preferred embodiments of the present invention, and in which.

DESCRIPTION OF THE PREFERRED EMBODIMENT

The method and apparatus of the present invention may be used in conjunction with any gas that undergoes a temperature change when reacted to produce a by-product, such as another gas. Any such gas that undergoes a temperature change is referred to herein as a reactive gas. The reactive gas may produce heat when the by-product is formed or it may adsorb heat when the by-product is formed. The instant invention provides a thermomechanical means for measuring this heat differential and providing the concentration of the reactive gas. A preferred example of such a reactive gas is ozone, which releases heat energy when it comes in contact with a suitable catalyst, such as a blend of iron, manganese, and tin oxide, to form oxygen, all as is well known to those skilled in the art.

Figure 1:
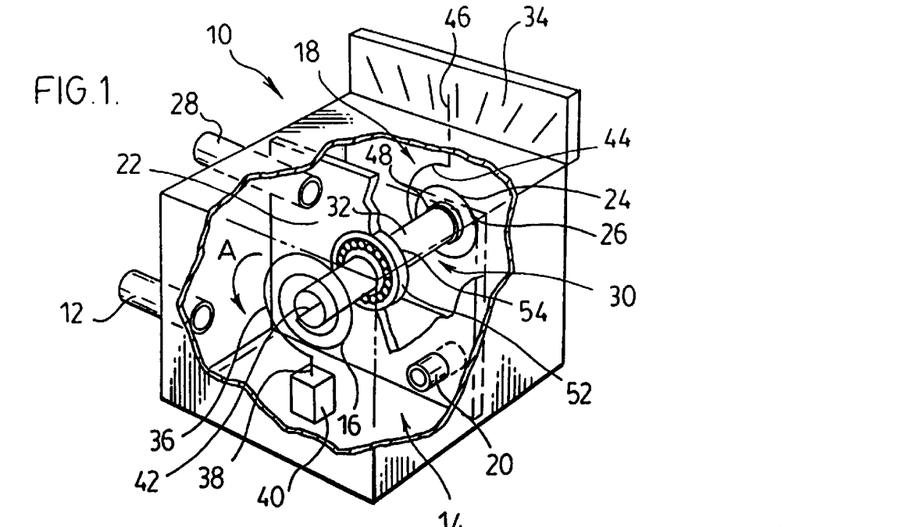
FIG. 1 is a perspective view, partly cut away, illustrating an apparatus for this invention.

A preferred apparatus 10 of this invention for measuring heat energy generated during conversion of a reactive gas, such as ozone, by a catalyst independent of the temperature of a gas mixture containing the reactive gas, is shown in FIG. 1. In particular, a gas stream containing a reactive gas is introduced through a conduit 12 to a first chamber 14 having at least one temperature sensor 16 for measuring the temperature of the gas mixture within first chamber 14. The gas stream may consist essentially only of the reactive gas. Alternately, the reactive gas may be present with a mixture of one or more non-reactive gasses.

Figure 4:
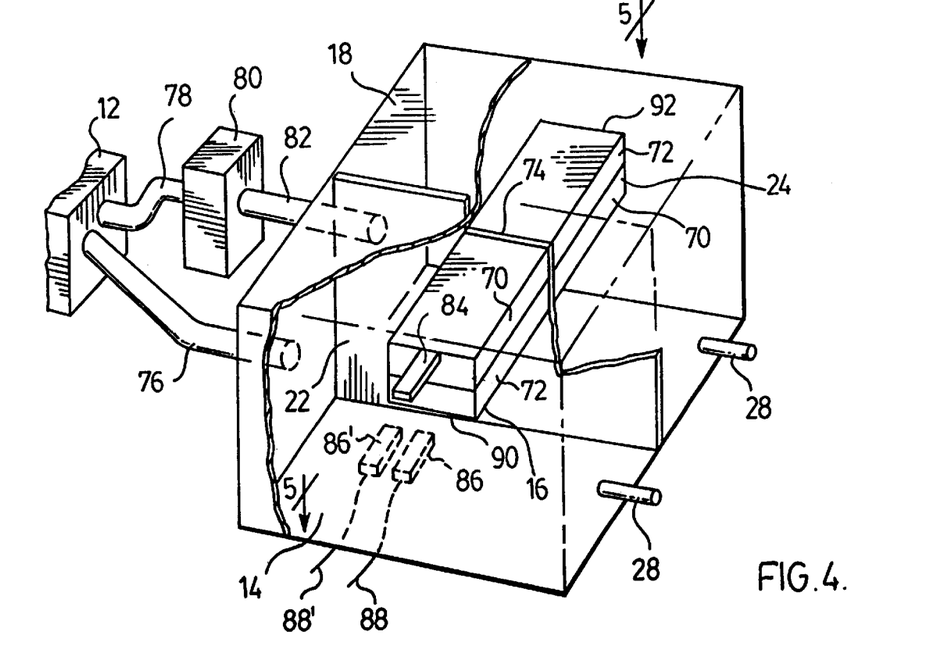
FIG. 4 is a perspective view, partly cut away, of a further alternative embodiment of the apparatus of FIG. 1.
Figure 5:
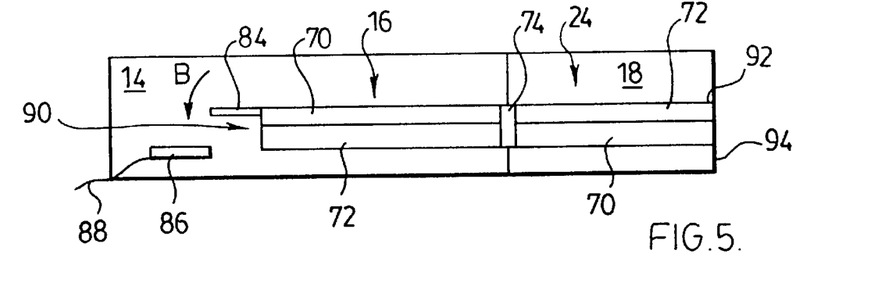
FIG. 5 is a cross section along the line 5—5 in FIG. 4.
Figure 6:
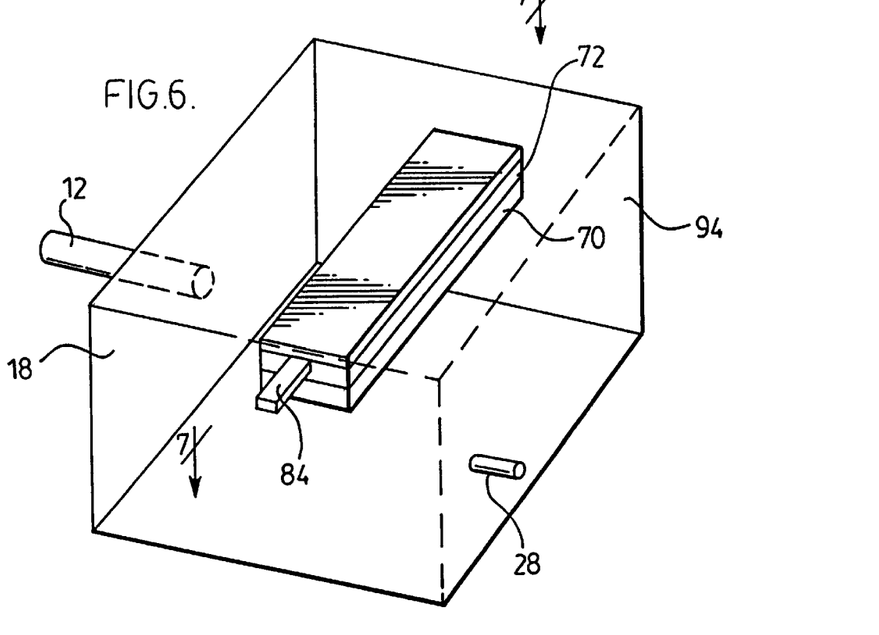
FIG. 6 is a perspective view, partly cut away, of a further alternative embodiment of the apparatus of FIG. 1: and, FIG. 7 is a cross section along the line 7—7 in FIG. 6.

Temperature sensor 16 may be any mechanical means that will move or shift position in response to the temperature of the gas mixture. Temperature sensor 16 may be in any particular orientation and of any particular configuration. For example, as shown in FIG. 1, temperature sensor 16 may be a helically wound member (eg, a spring). Thus, as temperature sensor 16 is heated or cooled, it will expand or contract in the circumferential direction (i.e. in the plane of the spring transverse to the axis of the spring). In the embodiment of FIGS. 4 and 5, first temperature sensor 16 is in the form of a longitudinally extending member. In either case, temperature sensor 16 produces a force (eg. angular or linear) in response to the temperature of the gas stream.

Preferably, first temperature sensor 16 is a bimetallic member. Bimetallic members are constructed from bimetallic materials so that the differential expansion of the materials in response to temperature changes causes the respective ends of the bimetallic member to be displaced as is well known to those skilled in the art. For example, in the embodiment of FIG. 1, temperature sensor 16 will be angularly displaced such as in the direction of arrow A whereas in the embodiment of FIGS. 4 and 5, temperature sensor 16 will be vertically displaced, such as in the direction of arrow B.

Temperature sensor 16 produces a first measurement that represents the initial temperature of the gas mixture. This first measurement representing the initial temperature of the gas mixture could be displayed by a display (not shown), and the means by which such a display could be linked to temperature sensor 16 are well known to those skilled in the art.

In the preferred embodiment of FIG. 1, the gas mixture is then directed from first chamber 14 to a second chamber 18 via conduit 20. First chamber 14 is thermally insulated from. second chamber 18. For example, first chamber 14 and second chamber 18 may be divided by a wall 22 constructed of a suitable thermally insulating material. Other means to thermally separate chambers 14 and 18 from one another will be apparent to those skilled in the art.

Second chamber 18 has at least one temperature sensor 24 for measuring the temperature of the gas mixture within second chamber 18. temperature sensor 24 may be any mechanical means that will move or shift position in response to the temperature of the gas mixture and may be the same or different to temperature sensor 16. In this preferred embodiment of the invention, second temperature sensor 24 is also a spring and, preferably a bimetallic spring. Temperature sensor 24 produces a second measurement that represents the temperature of the gas mixture in the second chamber. The temperature of the gas mixture within the second chamber will be different to that in the first chamber, as will be explained below. This second measurement representing the temperature of the gas mixture in the second chamber could also be displayed by a display not shown), and the means by which such a display could be linked to temperature sensor 24 are well known to those skilled in the art.

A catalyst 26 15 se chamber 18 to convert the reactive gas within the gas mixture to release (or adsorb) heat energy. Catalyst 26 may be located at any position in second chamber 18 that will come into contact with the gas stream entering second chamber 18 so long as the heat energy released or adsorbed during conversion of the reactive gas heats or cools the gas mixture so that the new temperature of the gas stream can be measured by temperature sensor 24. For example, it may be provided as part of the downstream flow path of conduit 20 in second chamber 18 (not shown). Preferably, catalyst 26 is coated on temperature sensor 24.

Catalyst 26 may be any material which will cause the reactive gas to undergo a chemical conversion to produce the by product. When the reactive gas is ozone, the catalyst is preferably a mixture of iron, manganese, and tin oxide coated on temperature sensor 24. This mixture causes the ozone to undergo an exothermic reaction to form oxygen (the by-product). The heat produced by the reaction causes temperature sensor 24 to record a different (and in this case a higher) temperature. If the catalyst is placed in the flow stream of the gas upstream of temperature sensor 24, then the heat generated from this conversion heats the gas mixture within second chamber 18. Therefore temperature sensor 24 in second chamber 18 produces a second measurement that represents the temperature of the heated gas mixture. Alternately, if catalyst 26 is coated on temperature sensor 24, then the heat of reaction directly heats temperature sensor 24. Other suitable mixtures of a catalyst for ozone will be apparent to those skilled in the art. Further, suitable catalysts to release heat energy during conversion of other reactive gases are well known to those skilled in the art.

The heated gas mixture may exit second chamber 18 through conduit 28 for subsequent disposal or uses that would be known to those skilled in the art. Also, a pump could be provided (not illustrated in FIGS. 1 or 3) to drive or draw the gas mixture through the first and second chambers and the respective conduits, as would be apparent to those skilled in the art.

The first measurement representing the measurement of the initial gas temperature from temperature sensor 16 in first chamber 14 and the second measurement representing the measurement of the temperature of the heated gas mixture from temperature sensor 24 in second chamber 18 are combined to obtain a differential measurement. The measurements produced by first and second mechanical temperature sensors 16, 24 may be individually read (electronically or preferably on an analog scale). The individual readings may then be compared to provide a signal corresponding to the concentration of the reactive gas. In the case of an analog scale, this may be by subtracting one analog reading from another. Alternately, if first and second temperature sensors 16, 24 provide electrical signals, these signals may be sent, for example, to a comparator to provide a signal corresponding to the concentration of the reactive gas. Preferably temperature sensors 16, 24 are mechanically linked so as to provide a single signal indicative of the differential measurement that may be electronic or which may be read on an analog scale. In the case of an analog scale, the relative displacement may produce a reading on the analog scale which is the concentration of the reactive gas.

To this end, a differentiator 30 may be provided to combine the first measurement representing the measurement of the initial gas temperature from temperature sensor 16 in first chamber 14 with the second measurement representing the measurement of the temperature of the heated gas mixture from temperature sensor 24 in second chamber 18 to obtain a differential measurement. In the preferred embodiment of FIGS. 1–3 differentiator 30 comprises a rotatably mounted shaft 32. The differential measurement represents a measurement of the heat generated during conversion of the reactive gas by the catalyst and can be displayed by a suitable display 34, which is preferably an analog scale. Further, as the amount of heat released or adsorbed for a given unit of reactive gas which is converted to a by-product is known, display 34 can be calibrated to show the concentration of the reactive gas within the gas mixture.

To ensure that the differential measurement obtained is independent of the initial temperature of the gas mixture, temperature sensors 16 and 24 in the first and second chambers 14 and 18, respectively, are calibrated so that when there is no reactive gas within the gas stream flowing through the chambers, the differential measurement obtained by differentiator 30 from combining the respective first and second measurements is constant. The constant measurement is preferably zero. In general, if there is no reactive gas within the gas mixture, there is no conversion by the catalyst in the second chamber to generate heat energy. Accordingly, the temperature of the gas mixture in second chamber 18 is the same as the temperature of the gas mixture in first chamber 14. In the preferred embodiment, temperature sensor 16 in first chamber 14 and temperature sensor 24 in second chamber 18 are calibrated so that if there is no reactive gas within the gas mixture the respective first and second measurements produced are equal. Further, in the preferred embodiment, temperature sensor 16 and temperature sensor 24 are arranged so that the respective first and second measurements cancel each other out when combined by differentiator 30 to produce a differential measurement of zero, as will hereinafter be explained. By having a differential measurement of zero which is independent of the temperature of the gas mixture when there is no reactive gas, then any differential measurement obtained when there is reactive gas within the gas mixture is representative only of the temperature of the heat energy released during conversion of the reactive gas.

Figure 2:
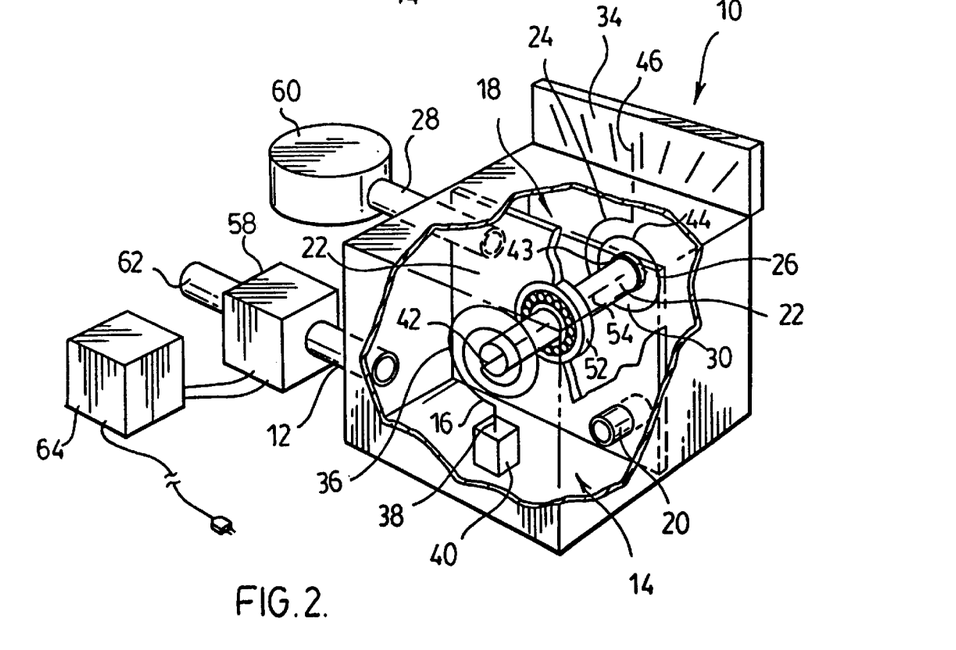
FIG. 2 is a perspective view, partly cut away, of the apparatus of FIG. 1, including additional components to produce the reactive gas.
Figure 3:
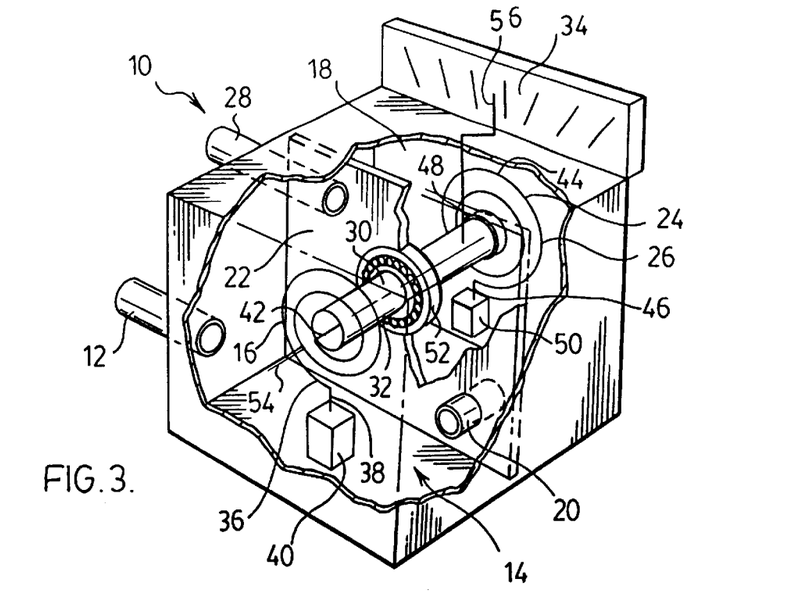
FIG. 3 is a perspective view, partly cut away, of an alternative embodiment of the apparatus of FIG. 1.

As previously mentioned, in a preferred embodiment of FIGS. 1–3, first temperature sensor 16 in first chamber 14 is a spring 36. Spring 36 has a first end 38 fixed within first chamber 14, for example, to a post 40 within the first chamber. Other suitable means for securing first end 38 within first chamber 14 would be known to those skilled in the art. It can be appreciated that with first end 38 fixed within chamber 14, the second end 42 is angularly displaced in relation to first end 38 in response to the expansion of the metal comprising the spring as it measures the initial temperature of the gas mixture in the first chamber. This angular displacement of second end 42 of spring 36 represents the initial temperature (the first measurement) of the gas mixture in the first chamber 14. End 42 is drivingly linked to rotatable shaft 32.

Similarly second temperature sensor 24 is a spring 44. Spring 44 has a first end 46 and a second end 48 which is angularly displaced with respect to first end 46 in response to the temperature of the heated gas mixture within second chamber 18. In the embodiment of this invention shown in FIG. 1 first end 46 provides a reading on analog scale 34 and second end 48 of spring 44 is drivenly linked to differentiator 30. Ends 48 and 42 may be affixed to rotatable shaft 32 by any means such as an adhesive, mechanical means (eg. a screw), or they may be received in a bore in shaft 32, or the like.

Differentiator 30, in the preferred embodiments illustrated in FIGS. 1 and 3, is a rotatable shaft 32 that extends from first chamber 14 through wall 22 to second chamber 18. Rotatable shaft 32 preferably does not transmit any significant heat between the chambers. Accordingly, shaft 32 is preferably made of a thermally nonconductive material (eg. wood). Alternately, shaft 32 may be composed of two member each of which is thermally conductive (eg. they may be made of metal) which are non-rotatably affixed to each other by means of an insulating material. Rotatable shaft 32 is rotatably mounted in chambers 14, 18 by any means. For example, wall 22 may be provided with a nylon member having an opening for rotatably receiving shaft 32. Alternately, as shown in FIG. 1, shaft 32 is held in position by a roller bearing assembly 52 that allows shaft 32 to rotate about a longitudinal axis 54.

Referring now to the embodiment illustrated in FIG. 1, since first end 38 of spring 36 is fixed within first chamber 14 to, for example, post 40, then only second end 42 of spring 36 is angularly displaced in response to the expansion or contraction of spring 36. Second end 42 of spring 36 is linked to one end of rotatable shaft 32 so that any angular displacement of end 42 in response to the differential expansion of the metals in the spring as it measures the initial temperature of the gas mixture in the first chamber tends to rotate shaft 32 about longitudinal axis 54 in one direction by an amount corresponding to the initial temperature of the gas stream in first chamber 14 (the first measurement). Second end 48 of spring 44 is linked to the other end of rotatable shaft 32 such that its angular displacement is in an opposite direction to the direction imparted to rotatable shaft 32 by second end 42 of spring 36 in first chamber 14. In this embodiment, first end 46 of spring 44 is free to be angularly displaced in relation to second end 48. The amount of the angular displacement of free first end 46 relative to second end 48 in response to the expansion of the spring 44 as it measures the temperature of the heated gas mixture in second chamber 18 represents the temperature of the heated gas mixture (the second measurement) in second chamber 18.

In use, a gas stream containing a reactive gas is fed to first chamber 14 via conduit 12. The gas stream is at a first temperature and causes temperature sensor 16 to expand or contract in a first direction. As end 38 is fixed in position, the expansion or contraction of temperature sensor exerts an rotational force in a first direction (eg. clockwise) on shaft 32 via end 42 that represents the initial temperature of the gas mixture in first chamber 14. This causes a consequential rotation of shaft 32 and therefore end 48 of temperature sensor 24. The gas stream is then fed to chamber 18 via conduit 20 wherein at least a portion of the reactive gas reacts to form a by-product and a temperature change. This temperature change causes end 46 to rotate relative to shaft 32 and end 48 in the opposite direction to that exerted by temperature sensor 16 (eg. counter clockwise). Thus end 46 provides an analog readout which may correspond to the concentration of the reactive gas in the gas stream or which may be the actual concentration of the reactive gas in the gas stream. The gas stream is vented from chamber 18 via conduit 28.

In the preferred embodiment of FIG. 3, first end 46 is fixed in position in second chamber 18, such as by being affixed to post 50. Second end 48 of spring 44 is drivingly connected by any means known in the art to the other end of rotatable shaft 32 so that any angular displacement of end 48 in response to the expansion of spring 44 as it measures the temperature of the heated gas mixture in the second chamber tends to rotate shaft 32 about longitudinal axis 54 in an opposite direction to the direction imparted by second end 42 of spring 36 in the first chamber. The amount that second end 48 is angularly displaced represents the temperature of the heated gas mixture in second chamber 18 (the second measurement). Rotatable shaft 32 combines the angular displacement of second end 42 (the first measurement) of spring 36 in one direction and the angular displacement of second end 48 (the second measurement) of spring 44 in an opposite direction to obtain a net rotation of shaft 32 (the differential measurement). This net rotation represents a measurement of heat generated during conversion of the reactive gas by the catalyst. An arm 56 may be secured to rotatable shaft 32 to show the net rotation of shaft 32 on display 34. Using known relationships between heat generated during conversion of a reactive gas, such as ozone, and the concentration of the reactive gas within the gas mixture, display 34 can be calibrated so display 34 is a read out of the concentration of the reactive gas.

Once again, if there is no reactive gas within the gas mixture, then there is no conversion by the catalyst in the second chamber to generate heat energy thus producing a differential measurement of preferably zero (i.e. there is no net movement of arm 56 on display 34).

FIG. 2 illustrates an embodiment of the invention similar to that illustrated in FIG. 1, but includes a generator 58 for converting a portion of a specific gas in the gas mixture to an associated reactive gas. In this way, apparatus 10 could be used to measure the temperature of a non-reactive gas by measuring the temperature of a corresponding reactive gas. For example, apparatus 10 could be used to measure the concentration of oxygen in a gas stream by converting the oxygen (or a known portion of it) to ozone and them measuring the heat produced during the conversion of ozone to oxygen as it passes through apparatus 10.

A pump 60, connected to second chamber 18 by conduit 28, draws the gas mixture into generator 58 through a conduit 62 from a supply of the gas mixture (not shown) for conversion of a portion of a specific gas to an associated reactive gas, then through conduit 12 into first chamber 14 of apparatus 10, then through conduit 20 into second chamber 18, before exiting through conduit 28. A power supply 64 may be connected to generator 58, all as is well known to those skilled in the art.

Generator 58 may be calibrated to display the amount of heat generated (or adsorbed) by the process, the concentration of the reactive gas (eg. ozone) in the flow stream or preferably the concentration of the specific gas (eg. oxygen). For example, a generator 58 may convert a known percentage of oxygen in an air flow stream to ozone. Using this information and the relationship between heat produced per unit weight of ozone converted to oxygen in apparatus 10, display 34 may display the concentration of the specific gas within the gas mixture fed to generator 58.

It can be appreciated that a generator 58 as provided in FIG. 2, can also be provided to the embodiment illustrated in FIG. 3, or other alternatives, as would be known to those skilled in the art.

It will also be appreciated that the reactive gas could be an oxide of nitrogen and display 34 could be a read out of the concentration of $NO_x$ in the flow stream (in the embodiment of FIG. 1) or of nitrogen (in the embodiment of FIG. 3).

An alternate preferred embodiment is shown in FIGS. 4 and 5. In this embodiment, mechanical temperature sensors 16 and 24 each comprises a longitudinally extending bimetallic strip consisting of a first metal 70 having a first coefficient of expansion and a second metal 72 having a second coefficient of expansion which is different to that of first metal 70. Sensors 16 and 24 are separated by an insulating material 74. A gas mixture is fed from a conduit 12 to first conduit 76 and second conduit 78. The gas mixture in second conduit 78 is fed to a catalyst bed 80 and then to second chamber 18 via conduit 82. The gas mixture which is fed to chamber 14 is at a first temperature and the gas mixture which is fed to chamber 18 is at a second temperature. Temperature sensor 16 is provided with a contact member 84. Chamber 14 is provided with two contact members 86 and 86' which are each electrically connected to a circuit (not shown) via wires 88 and 88' respectively. When contact member 84 contacts members 86 and 86' it completes a circuit.

Wall 22 is made of an insulating resilient member or it may include a portion surrounding insulating material 74 which is resilient and insulating so as to allow sensors 16 and 24 to move freely due to temperature changes in chambers 14 and 18 and so as to effectively insulate chambers 14 and 18 so that the increased temperature in one does not heat the other to a significant degree.

The position of the metals is reversed in each chamber 14, 18 so as to cause opposed movement of sensors 16 and 24. As shown, first metal 70 is positioned above second metal 72 in chamber 14 while second metal 72 is positioned above first metal 70 in chamber 18. Provided that an equal amount of each metal is used in each sensor 16, 24, there is no net movement of end 90 of sensor 16 when there is no reactive gas in the flow stream.

When a stream containing a reactive gas (eg. ozone) is fed to the apparatus, a portion will travel through the catalyst bed 80 and become heated. The gas stream entering chamber 18 will cause differential expansion of sensor 24. End 92 of sensor 24 is affixed to wall 94. Assuming that the metal with the higher coefficient of expansion is second metal 72, the heating of sensor 24 will exert an downward force on sensor 24 thereby bowing it downwardly and therefore displacing end 90 of sensor 16 downwardly (see arrow B). As the position of the metals are reversed in sensor 16, the temperature of the gas in chamber 14 (which has not been exposed to the catalyst) causes sensor 16 to bow upwardly. Thus sensor 16 may again provide a reverse force to compensate for the temperature of the gas in conduit 12. As the concentration of reactive gas increases, the net downward movement of end 90 and therefore contact member 84 increases. When the concentration of the reactive gas reaches a preset amount, contact member 84 contacts members 86, 86' thus completing a circuit and providing effectively an electronic signal that the preset concentration has been reached. The circuit may issue a warning (eg a sound or a light) or it could shut the system down, cause a valve to open further or take such other corrective action as may be required.

Figure 7:
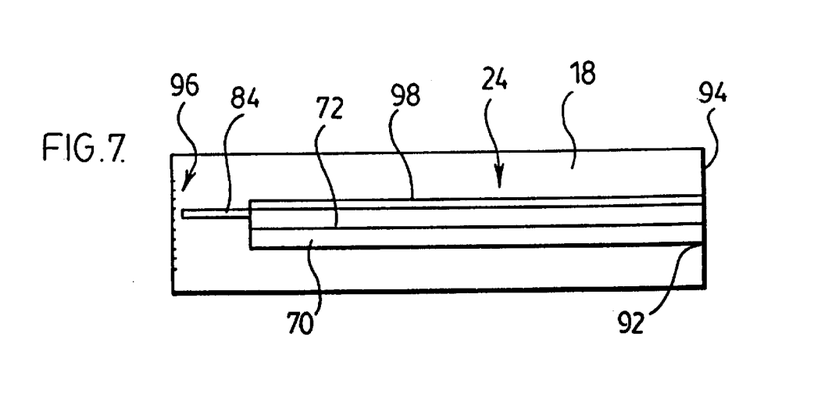

It will be apparent to those skilled in the art that member 84 could be a mechanical pointer for use with an analog display 96 as is shown in FIG. 7. It will also be appreciated that in the embodiment of FIGS. 4 and 5 that the catalyst could be provided in chamber 18 (eg. it could be coated on sensor 24). In this way conduit 12 could be split into two equal flow streams 76 and 78 which would lead respectively to chambers 14 and 18. In a further alternate embodiment, the apparatus could be to measure the concentration of a specific gas and catalyst chamber 80 could be replaced by or include a generator 58 to convert the specific gas to a reactive gas.

It will also be appreciated that if the heat produced or adsorbed by the conversion of the reactive gas to the by-product at the concentrations to be measured is substantial, then correcting for the ambient air temperature may not be necessary for a usable gas sensor. For example, the sensor could be set to read zero at room temperature. In such a case only a single sensor (eg. sensor 24) may be incorporated in a single chamber (eg. chamber 24). For example see FIG. 7. In this embodiment, the catalyst 98 is provided on the top surface of sensor 24.

It can be appreciated that variations to this invention would be readily apparent to those skilled in the art, and this invention is intended to include those alternatives.

We claim:

1. An apparatus comprising:
   (a) a catalyst positioned in an air flow path of a gas mixture containing a reactive gas, the reactive gas undergoing a reaction to produce a reacted gas that includes at least a by product and a change in heat upon exposure to the catalyst;
   (b) a reacted gas temperature sensor which is in thermal communication with at least one of the catalyst and the reacted gas and which undergoes movement with changes in temperature to which it is exposed to produce a reacted gas measurement representing the change in heat produced by the reaction of the reactive gas; and,
   (c) a display, the reacted gas temperature sensor is mechanically coupled to the display whereby movement of the reacted gas temperature sensor produces a signal on the display.

2. An apparatus according to claim 1 wherein the measurement is calibrated to represent the concentration of the reactive gas within the gas mixture.

3. An apparatus according to claim 1 wherein the temperature sensor includes an indicator, and the display comprises an analog display which is calibrated to represent the concentration of the reactive gas within the gas mixture and the measurement comprises the movement of the indicator due to the change in temperature of the temperature sensor.

4. An apparatus according to claim 1 wherein the signal is an electronic signal.

5. An apparatus according to claim 1 wherein the gas mixture comprises a specific gas and the apparatus further comprises a generator positioned upstream of the catalyst for converting at least a portion of the specific gas to the reactive gas.

6. An apparatus according to claim 5 wherein the temperature sensor includes an indicator, and the display comprises an analog display which is calibrated to represent the concentration of the reactive gas within the gas mixture and the measurement comprises the movement of the indicator due to the change in temperature of the temperature sensor.

7. An apparatus according to claim 6 wherein the specific gas is nitrogen or oxygen.

8. An apparatus according to claim 1 further comprising:
   (a) an ambient temperature chamber for receiving at least a portion of the gas mixture, the ambient temperature chamber having an ambient temperature sensor which undergoes movement with changes in temperature to which it is exposed to produce an ambient measurement representing the ambient temperature of the gas mixture;
   (b) a second chamber in which the reacted gas temperature sensor is positioned; and,
   (c) a differentiator to produce a differential measurement that represents a measurement of the heat generated during conversion of the reactive gas by the catalyst independent of the ambient temperature of the gas mixture containing the reactive gas.

9. An apparatus according to claim 8 wherein the ambient and reacted gas temperature sensors are calibrated so that when there is no reactive gas within the gas mixture the ambient measurement and the reacted gas measurement produce a differential measurement of zero.

10. An apparatus according to claim 8 wherein the differential measurement is calibrated to represent the concentration of the reactive gas within the gas mixture.

11. An apparatus according to claim 8 further comprising a divider having two outlets, one of which is in air flow communication with the ambient chamber and the other of which is in air flow communication with the reacted gas chamber.

12. An apparatus according to claim 8 further comprising an air inlet to the ambient chamber, a passageway connecting the chambers in air flow communication and an air outlet from the reacted gas chamber whereby the gas mixture passes sequentially through the ambient chamber and then the reacted gas chamber.

13. An apparatus according to claim 8 wherein the ambient measurement and the reacted gas measurement are electronic signals which are combined by the differentiator to produce the differential measurement.

14. An apparatus according to claim 8 wherein the measurements are opposed forces which are exerted on the differentiator to produce a net movement of the differentiator which is the differential measurement.

15. An apparatus according to claim 14 wherein the display is an analog display and an indicator is associated with the analog display and drivenly connected to one of the temperature sensors or the differentiator.

16. An apparatus according to claim 15 wherein the analog display is calibrated to represent the concentration of the reactive gas within the gas mixture.

17. An apparatus according to claim 8 wherein the gas mixture comprises a specific gas and the apparatus further comprises a generator positioned upstream of the catalyst for converting at least a portion of the specific gas to the reactive gas.

18. An apparatus according to claim 17 wherein the specific gas is nitrogen or oxygen.

19. An apparatus according to claim 1 wherein the catalyst is provided on the reacted gas temperature sensor.

20. An apparatus comprising:
   (a) a catalyst positioned in an air flow path of a gas mixture containing a reactive gas, the reactive gas undergoing a reaction to produce a reacted gas including at least a by product and a change in heat upon exposure to the catalyst;

(b) a reacted gas thermomechanical sensing means in thermal communication with at least one of the catalyst and the reacted gas for producing a movement of at least a portion of the sensing means due to changes in temperature to which it is exposed; and (c) the movement being mechanically translated to cooperate with an indicating means for providing a readout corresponding to the concentration of the reactive gas in the gas mixture.

21. An apparatus according to claim 20 wherein the indicating means provides a readout of the concentration of the reactive gas in the gas mixture.

22. An apparatus according to claim 21 wherein the indicating means provides a readout on an analog scale.

23. An apparatus according to claim 20 wherein the gas mixture comprises a specific gas and the apparatus further comprises a means positioned upstream of the catalyst for converting at least a portion of the specific gas to the reactive gas.

24. An apparatus according to claim 20 further comprising an ambient thermomechanical sensing means for contacting at least a portion of the gas mixture which has not been exposed to the catalyst and producing movement of at least a portion of the sensing means due to changes in temperature to which it is exposed.

25. An apparatus according to claim 24 wherein the movement of each sensing means produces an electronic signal which are combined by the indicating means to produce the readout.

26. An apparatus according to claim 24 wherein the movement of each sensing means produces opposed forces which cause the indicating means to move by a net amount to provide the readout.

27. An apparatus according to claim 26 wherein the indicating means provides a readout on an analog scale.

28. An apparatus according to claim 24 wherein the gas mixture comprises a specific gas and the apparatus further comprises a means positioned upstream of the catalyst for converting at least a portion of the specific gas to the reactive gas.

29. A gas sensor for measuring the concentration of a selected gas in a gas stream which is at an initial temperature comprising:

(a) a display;

(b) a mechanical indicator member, the display providing a measurement being in response to movement of the mechanical indicator member;

(c) a catalyst positionable in at least a portion of the gas stream, the catalyst being at an initial temperature prior to exposure to the gas stream, the catalyst, upon exposure to the selected gas, producing a change in temperature of at least one of;
   i. at least a portion of the catalyst to produce a catalyst at a second temperature which is different than the initial temperature of the catalyst; and
   ii. at least a portion of the gas stream at a second temperature which is different than the initial temperature of the gas stream; and (d) a mechanical gas temperature sensor in thermal communication with at least one of the catalyst at the second temperature and the gas stream at the second temperature and having a moveable portion, the moveable portion moving due to a temperature change in the gas temperature sensor and mechanically linked to the indicator member.

30. The gas sensor according to claim 28 wherein the display is an analog display and the indicator member moves relative to the display to provide a reading.

31. The gas sensor according to claim 28 wherein the display is electronic and the indicator member is mechanically coupled to the display to produce a reading.

32. The gas sensor according to claim 28 wherein the display is digital.

33. The gas sensor according to claim 28 wherein the catalyst is provided on the gas temperature sensor.

34. The gas sensor according to claim 28 further comprising a mechanical ambient temperature sensor positionable in at least a portion of the gas stream, the ambient temperature sensor undergoing movement with changes in temperature to which it is exposed and the ambient temperature sensor is coupled to the temperature sensor whereby the display provides a measurement based on the heat generated during conversion of the selected gas by the catalyst independent of the ambient temperature of the gas stream containing the selected gas.

35. The gas sensor according to claim 34 wherein the ambient gas temperature sensor is mechanically coupled to the gas temperature sensor.

36. A switch comprising:

(a) an electrical contact;

(b) a catalyst postionable in at least a portion of a gas stream, the catalyst being at an initial temperature prior to exposure to the gas stream and the gas stream is at an initial temperature prior to exposure to the catalyst, the catalyst, upon exposure to the gas stream, producing a change in temperature of at least one of;
   i. at least a portion of the catalyst to produce a catalyst at a second temperature which is different than the initial temperature of the catalyst; and
   ii. at least a portion of the gas stream at a second temperature which is different than the initial temperature of the gas stream; and (c) a mechanical gas temperature sensor positionable in at least a portion of a gas stream, in thermal communication with at least one of the catalyst at the second temperature and the gas stream at the second temperature and having an electrically conductive portion which is moveable to engage the electrical contact due to a temperature change in the gas temperature sensor, the moveable portion completing a circuit when it contacts the electrical contact.

37. The switch according to claim 36 wherein the catalyst is provided on the gas temperature sensor.

38. The switch according to claim 36 further comprising a mechanical ambient temperature sensor positionable in at least a portion of the gas stream, the ambient temperature sensor undergoing movement with changes in temperature to which it is exposed and the ambient temperature sensor is coupled to the temperature sensor whereby the sensor readout provides a measurement based on the heat generated during conversion of the selected gas by the catalyst independent of the ambient temperature of the gas stream containing the selected gas.

39. The switch according to claim 38 wherein the ambient gas temperature sensor is mechanically coupled to the gas temperature sensor.

40. An apparatus according to claim 1 wherein the reacted gas temperature sensor comprises a bimetallic member.

41. An apparatus according to claim 20 wherein the reacted gas thermomechanical sensing means comprises a bimetallic member.

42. A gas sensor according to claim 28 wherein the mechanical gas temperature sensor comprises a bimetallic member.

43. A switch according to claim 36 wherein the mechanical gas temperature sensor comprises a bimetallic member.

* * * * *